US010640449B2

(12) United States Patent
Atkins et al.

(10) Patent No.: US 10,640,449 B2
(45) Date of Patent: May 5, 2020

(54) METHODS OF USING N-OXYL POLYMERIZATION INHIBITOR IN A WASH SETTLER FOR PREPARING METHYL METHACRYLATE

(71) Applicants: Dow Global Technologies LLC, Midland, MI (US); Rohm and Haas Company, Collegeville, PA (US)

(72) Inventors: Joseph Atkins, Manvel, TX (US); Philippe P. Maillot, Kingwood, TX (US); Joy L. Mendoza, Seabrook, TX (US); Alan E. Sopchik, Seabrook, TX (US); Mingyu Ye, Deer Park, TX (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/466,849

(22) PCT Filed: Dec. 8, 2017

(86) PCT No.: PCT/US2017/065297

§ 371 (c)(1),
(2) Date: Jun. 5, 2019

(87) PCT Pub. No.: WO2018/118461

PCT Pub. Date: Jun. 28, 2018

(65) Prior Publication Data

US 2019/0345093 A1 Nov. 14, 2019

Related U.S. Application Data

(60) Provisional application No. 62/436,699, filed on Dec. 20, 2016.

(51) Int. Cl.

| | |
|---|---|
| ***C07C 67/62*** | (2006.01) |
| ***C07C 67/58*** | (2006.01) |
| ***C07C 69/54*** | (2006.01) |

(52) U.S. Cl.
CPC .............. *C07C 67/62* (2013.01); *C07C 67/58* (2013.01); *C07C 69/54* (2013.01)

(58) Field of Classification Search
CPC .......... C07C 67/62; C07C 67/58; C07C 69/54
See application file for complete search history.

(56) References Cited

U.S. PATENT DOCUMENTS

| | | | |
|---|---|---|---|
| 9,388,188 B2 | 7/2016 | Starcevic et al. | |
| 2013/0178652 A1 | 7/2013 | Fruchey et al. | |
| 2016/0251297 A1* | 9/2016 | Bernardin ............. | B01D 3/143 203/8 |

FOREIGN PATENT DOCUMENTS

| | | |
|---|---|---|
| CN | 103254091 * | 4/2015 |
| EP | 0685447 A2 | 12/1995 |
| EP | 0765856 A1 | 4/1997 |

* cited by examiner

*Primary Examiner* — Paul A Zucker
(74) *Attorney, Agent, or Firm* — Andrew E. Merriam

(57) ABSTRACT

The present invention provides methods comprising washing or, preferably, washing and neutralizing a sulfur acid containing crude MMA stream to generate a two phase stream containing at least methacrylic acid, methacrylamide (MAM), water and methanol, and an organic component containing methyl methacrylate and thereby form an aqueous component; including in any of the organic component, the aqueous component of a neutralized sulfur acid containing crude methyl methacrylate (MMA) stream or the organic component of a neutralized sulfur acid containing crude methyl methacrylate (MMA) stream one or more N-oxyl compound polymerization inhibitor; followed by separating the aqueous component from the organic component, thereby forming a treated crude MMA stream and an aqueous stream to remove residual (meth) acrylic acid.

10 Claims, 1 Drawing Sheet

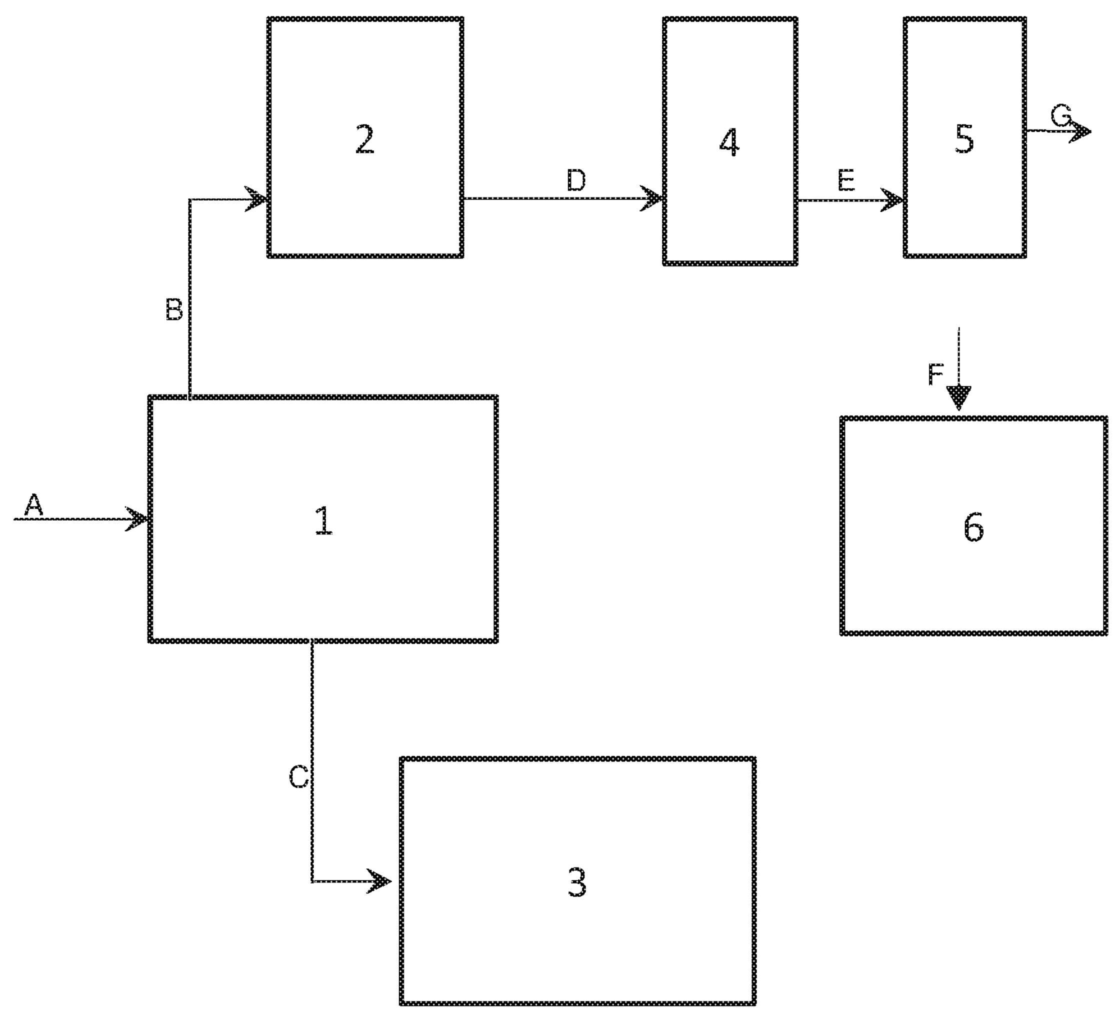
2
D
4
E
5
G
B
F
A
1
6
C
3

METHODS OF USING N-OXYL POLYMERIZATION INHIBITOR IN A WASH SETTLER FOR PREPARING METHYL METHACRYLATE

The present invention relates to methods comprising adding one or more N-oxyl compound polymerization inhibitors to a sulfur acid salt containing crude methyl methacrylate (MMA) stream containing methacrylic acid (MAA), methacrylamide (MAM), and methanol, preferably, after neutralizing the sulfur acid containing crude methyl methacrylate (MMA) stream with an aqueous base.

Various synthetic routes are known in the formation of methyl methacrylate (MMA) and include known purification of crude MMA streams. In the production of MMA, crude MMA streams can be purified by distillation or by extraction. No matter the route or purification used, MMA producers desire to maximize MMA yield by recovering byproducts of the esterification reaction such as methacrylic acid (MAA) for further esterification. The product and by-product streams formed in the making of MMA include monomers, including MMA, MAA and methacrylamide (MAM) which can polymerize in the process and require inhibition. In process polymerization inhibitors have been added to prevent monomers from polymerizing; one drawback of common vinyl (meth)acrylate polymerization inhibitors is that they lack solubility both the in organic and aqueous streams.

U.S. Pat. No. 9,388,118 to Jaeger et al. discloses processes for preparing (meth)acrylates of $C_{10}$ alcohol mixtures (esters) by azeotropic distillation wherein the methods comprise neutralizing the esterification output with an alkaline solution, separating the resulting aqueous and organic phases of the esterification output, and then washing the organic stream. Jaeger discloses adding polymerization inhibitors to all process stages, wherein the polymerization inhibitor can comprise an N-oxyl compound. However, Jaeger discloses azeotropic distillation methods which lead to a need to remove organic solvents from the crude organic phase.

The present inventors have endeavored to improve the stability of streams that contain an organic and an aqueous layer and that have methyl (meth)acrylate monomer in the organic and methacrylic acid in the aqueous layer.

SUMMARY OF THE INVENTION

1. In accordance with the present invention, methods for removing methacrylic acid (MAA) and other by-products from a sulfur acid containing crude methyl methacrylate (MMA) stream from a reaction for making MMA which contains methacrylic acid, methacrylamide (MAM), methanol, a sulfur acid salt, for example, a sulfuric acid or a sulfonic acid salt of ammonia or an alkali metal, and containing methyl methacrylate, comprise including in the sulfur acid containing crude methyl methacrylate (MMA) stream one or more N-oxyl compound polymerization inhibitor, preferably, 4-hydroxy-2,2,6,6-tetramethylpiperidinoxyl (4-HT), preferably, in the including wherein the N-oxyl compound comprises an aqueous mixture or solution.

2. In accordance with the methods of the present invention as in item 1, above, further comprise neutralizing the sulfur acid containing crude MMA stream with aqueous base, preferably, aqueous ammonia, to generate a two phase stream having a neutralized aqueous component containing at least a methacrylic acid salt, preferably, ammonium methacrylate ($NH^4$+$MAA^-$), methacrylamide (MAM), water, methanol, a sulfur acid salt, preferably, sulfuric acid salt or sulfate, or, more preferably, ammonium sulfate, an ammonium salt, and an organic component containing methyl methacrylate, followed by including the one or more N-oxyl compound polymerization inhibitor effective in both the aqueous component and the organic component, preferably, 4-hydroxy-2,2,6,6-tetramethylpiperidinoxyl (4-HT), in the neutralized aqueous component or the organic component, or both, optionally, followed by separating the neutralized aqueous component from the organic component, thereby forming a treated crude MMA stream and a neutralized aqueous stream which comprises ammonium methacrylate or another (meth) acrylic acid salt.

3. In accordance with the methods of the present invention as in items 1, or 2, above, wherein the including of the polymerization inhibitor further comprises adding a second inhibitor chosen from aromatic amines, such as aromatic diamines or aryl alkyl amines; thiazine containing compounds, such as phenothiazine; nitrosophenols, such as 4-nitrosophenol; 4-hydroxy-2,3,6,6-tetramethylpiperidine; and mixtures thereof.

4. In accordance with the methods of the present invention as in any one of items 2, or 3, above, wherein the neutralizing comprises adding aqua ammonia to the sulfur acid containing crude methyl methacrylate (MMA) stream and the resulting pH ranges from 6 to 10, or, preferably, from 7 to 8.

5. In accordance with the methods of the present invention as in any one of items 2, 3, or 4, above, wherein, the separating takes place in a decanter or gravity separator wherein temperature ranges from 20 to 100° C., or, preferably, from 40 to 80° C., or, more preferably, from 20 to 40° C.

6. In accordance with the methods of the present invention as in any one of items 2, 3, 4, or 5, above, wherein the method comprises the neutralizing and washing with water the sulfur acid containing crude methyl methacrylate (MMA) stream prior to the including the N-oxyl compound polymerization inhibitor and then separating the neutralized aqueous component from the organic component, thereby forming a treated crude MMA stream and a neutralized aqueous stream which comprises ammonium methacrylate and residual (meth) acrylic acid.

7. In accordance with the methods of the present invention as in any one of items 1, 2, 3, 4, 5, or 6, above, wherein the amount of the N-oxyl compound polymerization inhibitor included ranges from 10 to 5000 ppm, or, preferably, from 10 to 600, or, preferably, up to 100 ppm, based on the total weight of the stream to which it is added and the total polymerization inhibitor.

8. In accordance with the methods of the present invention as in any one of items 2, 3, 4, 5, 6, or 7, above, the methods further comprising adding one or more N-oxyl compound polymerization inhibitor, preferably, 4-hydroxy-2,2,6,6-tetramethylpiperidinoxyl (4-HT), to the two phase stream prior to the separating.

9. In accordance with the methods of the present invention as in any one of items 2 or 8, above, the methods further comprising removing the neutralized aqueous stream comprising methanol, MAM and ammonium methacrylate ($NH^4$+$MAA^-$), and ammonium sulfate after separating the organic component and the neutralized aqueous component of the two phase stream, thereby providing the treated crude MMA stream.

10. In accordance with the methods of the present invention as in any one of items 8 or 9, above, wherein, following the separating, the method further comprises adding one or more N-oxyl compound polymerization inhibitor, preferably, 4-hydroxy-2,2,6,6-tetramethylpiperidinoxyl (4-HT), to the treated crude MMA stream and feeding it to a second decanter or gravity separator or to multiple decanters or gravity separators for additional purification to remove residual (meth)acrylic acid or ammonium (meth) acrylate.

11. In accordance with the methods of the present invention as in item 10, above, wherein the methods further comprise adding one or more N-oxyl compound polymerization inhibitor, preferably, 4-hydroxy-2,2,6,6-tetramethylpiperidinoxyl (4-HT), to the treated crude MMA stream before feeding it to a second decanter or gravity separator or the multiple decanters or gravity separators.

12. In accordance with the methods of the present invention as in any one of items 1 to 11, above, further comprising, after washing and separating to form a treated crude MMA stream, condensing under reflux the treated crude MMA stream while including in reflux the one or more N-oxyl compound polymerization inhibitor.

13. In accordance with the methods of the present invention as in any one of items 1 to 12, above, wherein the sulfur acid containing crude MMA stream contains substantially no azeotroping solvent or entraining solvent.

14. In accordance with the methods of the present invention as in any one of items 2 to 12, above, further comprising recycling the neutralized aqueous stream for use in making additional methyl methacrylate.

15. In accordance with the methods of the present invention as in any one of items 2 to 13, wherein the neutralizing takes place in a loop for fluid recycling comprising a washing section, a neutralizing section, and a separating section.

14. In accordance with the methods of the present invention as in any one of items 10 or 11, above, wherein the feeding comprises feeding the treated crude MMA stream to a second wash settler before feeding it to, respectively, a second decanter or gravity separator or feeding the treated crude MMA stream to multiple wash settlers, each time before feeding it to a succeeding decanter or gravity separator.

15. In accordance with the methods of the present invention in accordance with any of items 1 to 14, above, wherein the only polymerization inhibitor in the neutralized aqueous component comprises an N-oxyl compound, preferably, 4-hydroxy-2,2,6,6-tetramethylpiperidinoxyl (4-HT).

16. In accordance with the methods of the present invention as in items 9 to 14, wherein the removing methods further comprise washing the treated crude MMA stream that contains the N-oxyl inhibitor a second time with water.

17. In accordance with the methods of the present invention as in any one of items 1 to 14 wherein the one or more N-oxyl compound polymerization inhibitor is added as a solution in water to any of the sulfur acid containing crude methyl methacrylate (MMA) stream, the sulfur acid salt containing crude methyl methacrylate (MMA) stream the neutralized aqueous component, or the treated crude MMA stream.

BRIEF DESCRIPTION OF THE DRAWING

The FIGURE is a schematic of a method of the present invention.

All percentage compositions are weight percentages (wt. %), and all temperatures are in ° C., unless otherwise indicated.

Unless otherwise indicated, all temperatures are room temperature (21-23° C.) and all pressures are standard pressure (~101 kPa or ~760 mm/Hg).

As used herein, "at least one" and "one or more" are used interchangeably. The terms "comprises," "includes," and variations thereof do not have a limiting meaning where these terms appear in the description and claims.

The singular forms "a," "an," and "the" include plural referents unless the context clearly dictates otherwise.

All phrases comprising parentheses denote either or both of the included parenthetical matter and its absence. For example, the phrase "(meth)acrylate" includes, in the alternative, acrylate and methacrylate.

As used herein, the term "aqueous gel permeation chromatography" or "aqueous GPC" refers to methods used to analyze indicated aqueous component materials and determine amounts of soluble polymer in the indicated crude MMA streams and neutralized aqueous streams wherein 50.0 [.IL of a stream sample is mixed ata 1:10 dilution factor in deionized (DI) water and injected into a Waters Alliance™ 2695 Separations Module (Waters Corporation, Milford, Mass.) equipped with a Waters Ultrahydrogel™ 120 column (7.8 ID×300 mm) containing poly (methyl methacrylate) standards having a range of molecular weights of from 1,000 to $1\times10^6$ and a Waters Refractive Index (RI) Detector, using 100 mM sodium nitrate (NaNO3) and 10 mM monopotassium phosphate (KH2PO4) at pH 9 in 18 ma MiIliQ™ (Agilent Corp., Santa Clara, Calif.) as a mobile phase.

As used herein, the term "high pressure liquid chromatography" or H PLC refers to methods used to analyze the indicated polymerization inhibitor in the indicated crude MMA streams and neutralized aqueous streams wherein 5.0 [.IL of a stream sample is mixed at a 1:10 dilution factor in dimethyl sulfoxide (DMSO) and injected into a Waters 2695 Separations Module (Waters Corp.) equipped with a Cortecs™ C18+ column (2.1×100 mm) containing 5.7 wt. % carbon loading, with carbon having a 90

A pore size at 25° C. and a 2996 Photo Diode Array Detector; tetrahydrofuran (THF) was used as the mobile phase.

As used herein, the term "ppm" means part per million by weight.

As used herein, the term "substantially the only polymerization inhibitor" means that a given polymerization inhibitor comprises at least 99 wt. %, or, preferably, at least 99.5 wt. % or, more preferably, at least 99.9 wt. % of all polymerization inhibitors in an indicated composition, method or use.

As used herein, the term "substantially no azeotroping solvent or entraining solvent" means less than 1000 ppm or, preferably, less than 500 ppm of any organic solvent which is not a reactant or a reaction by product in the making of methyl methacrylate in accordance with the present invention, such as toluene or hexanol.

As used herein, the term "sulfur acid" refers to a strong acid containing a sulfur atom and having a pKa of 2 or less or, preferably, 1 or less including, for example, sulfuric acid and organic sulfonic acids.

In accordance with the present invention, the inventors have discovered methods of purifying crude methyl methacrylate from reaction product streams wherein an N-oxyl compound is used as a polymerization inhibitor in the crude product stream, in particular during washing with water or after neutralizing with aqueous base. In the methods, the N-oxyl compound is soluble in both an organic and aqueous component of the crude product and experiments suggest that the N-oxyl compound can retard polymer formation in aqueous phase as well as in the organic phase by minimizing soluble polymer formation.

The present invention comprises methods of extraction by adding aqueous ammonia to neutralize a sulfuric acid containing crude methyl methacrylate (MMA) stream, which facilitates the removal of monomer byproducts such as (meth)acrylic acid, and to remove unwanted sulfate and sulfite salts. Ammonia converts (meth)acrylic acid to ammonium (meth)acrylate to aid in the removal of (meth)acrylic acid from the organic or MMA layer, which can polymerize. Accordingly, adding a free-radical inhibitor to prevent polymer buildup in the aqueous layer provides yield and purity enhancements in making crude MMA. N-oxyl compounds, such as 4-hydroxy TEMPO, act as polymerization inhibitors that are soluble in both the organic and aqueous layers that can mitigate polymer formation in both layers.

In the production of methyl methacrylate, bottoms streams comprise crude methyl methacrylate and are two phase compositions, which are feed streams in the purification methods of the present invention. Ammonia solutions are used to neutralize sulfur acid containing bottoms streams or feed streams having (meth)acrylic acid. Ammonia in water with the methacrylic acid forms ammonium methacrylate and neutralizes sulfuric acid, enabling the formation of ammonium sulfate and its removal from the bottom stream into an aqueous phase that can be readily separated from the bottoms stream by simple phase separation in a conventional separating method, such as separation by phases by drawing the organic phase down from the two phase feed stream. Generally, the reaction to make methyl methacrylate produces an organic phase containing methyl methacrylate, methanol, and methacrylic acid. The reaction also forms an aqueous phase comprising methanol and methacrylic acid as well as any water soluble monomer by product, such as methacrylamide or catalyst residues, such as sulfuric acid. Any reactant or catalyst used may form part of the by product. Unwanted side reactions include dimerization and polymerization of the monomers.

In accordance with the methods of the present invention, a sulfur acid containing crude methyl methacrylate (MMA) stream can be made by methods wherein acetone cyanohydrin (ACH) is hydrolyzed by sulfuric acid to produce a-hydroxyisobutyramide (HIBAM), and a-sulfatoisobutyramide (SIBAM). The HIBAM and the SIBAM are thermally converted to 2-methacrylamide (MAM) forming a cracked mix, which is fed to an MMA ester reactor with aqueous methanol to produce a crude MMA upper layer and an aqueous lower layer. After phase separating the two layers, the MMA upper layer is flashed and becomes a sulfur acid containing crude methyl methacrylate (MMA) stream. The method of the present invention comprises washing and/or neutralizing this sulfur acid containing crude methyl methacrylate (MMA) stream with water or aqueous base, such as aqueous ammonia to form a two phase stream of an aqueous component and an organic component, and separating the aqueous component to remove methacrylic acid (MAA) and other acid salts. Thus, separating of the two-phase streams takes place in a wash settler.

In the methods of the present invention, suitable N-oxyl-compounds are 4-hydroxy-2,2,6,6-tetramethylpiperidine N-oxyl, 4-oxo-2,2,6,6-tetramethylpiperidine N-oxyl, 4-methoxy-2,2,6,6-tetramethylpiperidine N-oxyl, 2,2,6,6-tetramethylpiperidine N-oxyl, 4-acetoxy-2,2,6,6-tetramethylpiperidine N-oxyl and 2,2,6,6-tetramethylpiperidine N-oxyl, preferably, 4-hydroxy-2,2,6,6-tetramethylpiperidine N-oxyl.

As shown in the FIGURE, showing a schematic of the present invention, the reactor effluent (A) from an esterification reactor is separated in a liquid-liquid phase separator (1) whereby the bottom stream (C), which is aqueous, is fed to a lower layer flash column (3) while the sulfur acid containing crude MMA rich upper layer or stream (B) is fed to a column (2) for reduction of process pressure. Column (2) comprises an overhead condenser (not shown) and lower bottom pump which draws sulfur acid containing crude MMA containing feed stream (D) which is pumped through a cooler (not shown) and a neutralization loop (4). The neutralization loop (4) comprises a pair of pumps providing a loop containing a static mixer (not shown), cooler (not shown) and pH meter (not shown) and into which aqua ammonia and the polymerization inhibitor is valved (not shown) to neutralize any acid and to maintain a desired pH. This results in the neutralized two phase stream of the present invention. The neutralized two phase stream (E) is pumped to a wash settler (5) comprising a gravity extractor that separates and removes from the two phase stream (E) a lower neutralized aqueous stream (F) comprising methanol, MAM and ammonium MAA, water, and ammonium sulfate and a sulfur acid containing crude methyl methacrylate stream (G). Prior to feeding the crude MMA to the subsequent wash settlers, additional water (not shown) and polymerization inhibitor (not shown) can be added. The lower neutralized aqueous stream (F) or neutralized aqueous stream from wash settler (5) is sent to a recycle tank (not shown). The upper layer (G) or treated organic component stream is treated crude MMA. Not shown in the FIGURE, an optional second or middle wash settler (MWS) and, optionally, a third or top wash settler (TWS) further extract MAA and other aqueous by products from the resulting product upper layers of crude MMA taken from, respectively, the BWS and the MWS. Also, if the MWS and TWS are used, the aqueous extract lower layer of each of the MWS and TWS is added to the recycle tank.

Suitable separators in a wash settler (5) can be used, such as a decanter or a simple gravity feed device allows separating the two phases of the two phase stream and the removal of the neutralized aqueous stream therefrom.

Concentrations of (meth)acrylic acid remaining in the treated crude methyl methacrylate (MMA) stream after neutralizing the two phase stream and separating the two phase stream in the extractor of the present invention range from 0 to 1 wt. %, or, preferably, from 0 to 0.5 wt. %, based on the total weight of MMA present in the initial two phase stream before processing it in accordance with the methods of the present invention.

EXAMPLES

In the Examples that follow, unless otherwise indicated, all pressures are standard pressure.

In the Examples that follow, the remaining concentrations of the indicated extract materials are determined by GPC for the concentration of aqueous soluble polymer and by HPLC for the concentration of 4-HT inhibitor was performed The following chemical abbreviations were used: MMA=methyl methacrylate; Me0H=methyl alcohol; MAA=methacrylic acid; 4-HT=4-hydroxy-2,2,6,6-tetramethylpiperidinoxyl; MAM=methacrylamide.

Example 1

The process as set forth in the FIGURE wherein the upper layer of an esterification reactor feed containing a feed stream of MMA, MeOH, MAA, MAM, and sulfuric acid was carried out in a trial that included wash settlers in three separate wash settler loops, each having a neutralizing locus where aqua ammonia is added to a sulfur acid containing crude methyl methacrylate (MMA) stream to form a neutralized two phase stream and wherein 4-HT is added as a 1 wt. % aqueous solution to the neutralized two phase stream. The wash settler loops are a bottom wash settler loop, a middle wash settler loop and a top wash settler loop. Table 1, below, gives the added amount of the indicated polymerization inhibitor added to the bottom wash settler loop to minimize the formation of poly(MAA), poly(MMA) and other aqueous and non-aqueous soluble polymers in the two phase stream.

Table 2, below, gives the amount of the indicated polymerization inhibitor added in the reflux line of a light ends column which is a light ends recovery column used to separate MMA from methanol and acetone or other volatiles. The bottoms or heavies from the light end columns contain MMA and an aqueous stream that has up to 2 wt. % MMA, also referred to as a treated crude MMA stream. In the treated crude bottom stream, the polymerization inhibitor minimizes the formation of poly(MMA) and other aqueous and non-aqueous soluble polymers, thereby inhibiting polymerization in both of the aqueous component and the organic component of the washed bottom streams in the light ends column separator.

TABLE 1

Bottom Wash Settler Extract

| | BWS Aqueous 4-HT (ppm) | BWS Aqueous Soluble Polymer (ppm) |
|---|---|---|
| BWS Extract | 27 | 12 |
| BWS Extract | 27 | 82 |
| BWS Extract | 34 | 85 |
| BWS Extract | 33 | 95 |
| BWS Extract | 24 | 84.3 |
| BWS Extract | 25.3 | 77.2 |
| BWS Extract | 30 | 51 |
| BWS Extract | 15.8 | 15.9 |
| BWS Extract | 14 | 91.2 |

TABLE 1

Light Ends Separator Extract

| Light Ends Aqueous 4-HT (ppm) | Light Ends Aqueous Soluble Polymer' ppm |
|---|---|
| 20.1 | ND |
| 38 | ND |
| 44 | ND |
| 17 | ND |
| 29 | ND |
| 30 | ND |
| 11 | ND |
| 18 | ND |
| 33 | ND |
| 33 | ND |
| 30 | ND |
| 48 | ND |
| 44 | ND |
| 45 | ND |
| 59.5 | ND |
| — | ND |
| 52.7 | ND |
| 16.3 | 11 |
| 30 | ND |

ND: Not detected or below the detection limit.

As shown in Tables 1 and 2, above, the methods of the present invention reduce the amount of water soluble polymer remaining in the aqueous component stream produced thereby. Not shown, no polymer was detected in the crude stream in the middle wash settler. The examples show that the N-oxyl compound polymerization inhibitor works in the aqueous phase. Further, the inventors did not observe any decrease in the active inhibitor in the organic component or any increase in the amount of soluble polymer in either the aqueous or the organic phase.

Example 2

Static Stability Testing

Glass tubes equipped as needed with a sparge outlet were loaded with a treated crude organic component from a third wash settler in a series of three wash settlers, and an aqueous feed from a bottom wash settler as configured in the FIGURE. The contents of each tube were heated in a temperature controlled bath wherein the temperature was controlled at 75° C. Examples were prepared by adding equal parts of both the organic and aqueous layer from the bottom wash settler, then adding the indicated amount of polymerization inhibitor to each tube, adding the indicated amount of polymerization inhibitor and shaking the tube by hand for roughly 1 minute to mix. Then the tubes were placed into the sparge assembly to sparge each sample with nitrogen. After 30 minutes, the sparge tube was removed and the tube capped and vented. Inert tubing was attached to the vent on the tube and connected to a manifold on the temperature controlled bath where a nitrogen purge was established at 1-2 bubbles/second to maintain a positive nitrogen atmosphere on the tube for the duration of the test. Periodically, the tubes were raised out of the temperature controlled bath, the cap removed and ~1 mL samples of both phases taken for testing. The top cap was then immediately replaced to maintain the nitrogen atmosphere. Both layers of each tube were analyzed for soluble polymer via gel permeation chromatography (GPC), as defined above. The results are presented in Tables 3 and 4, below.

TABLE 3

Static Stability Studies of the bottom wash settler Extract without 4-HT at 75° C.

Extract Layer Soluble Polymer (ppm) - No 4-HT Added

| Example | Time (hr) 0 | 20 | 45 |
|---|---|---|---|
| 2-1 | 398 | 4389 | 14691 |
| 2-2 | 373 | 6587 | 14199 |
| 2-3 | 1505 | 4877 | 16029 |
| 2-4 | 226 | 5922 | 12741 |
| 2-5 | 427 | 4923 | 17327 |
| 2-6 | 744 | 6523 | 10623 |
| 2-7 | 744 | 6523 | 10623 |

TABLE 4

Static Stability Studies of the bottom wash settler Extract with 4-HT at 75° C.

| Example | Time (hr) 0 | 20 | 45 |
|---|---|---|---|
| Extract Layer Soluble Polymer (ppm) - 50 ppm 4-HT Added | | | |
| 2-8 | 427 | 1033 | 1167 |
| 2-9 | 435 | 820 | 832 |

TABLE 4-continued

Static Stability Studies of the bottom wash settler Extract with 4-HT at 75° C.

| Example | Time (hr) 0 | 20 | 45 |
|---|---|---|---|
| Extract Layer Soluble Polymer (ppm) - 100 ppm 4-HT Added | | | |
| 2-10 | 226 | 791 | 638 |
| 2-11 | 427 | 1020 | 932 |
| 2-12 | 364 | — | 502 |
| 2-13 | 435 | 793 | 683 |

As shown in Tables 3 and 4 above, the methods of the present invention consistently and dramatically minimize the amount water soluble polymer formed in the aqueous component of a two phase feed stream even though the polymerization inhibitor was added to a two phase stream.

We claim:

1. A method for removing methacrylic acid (MAA) from a sulfur acid containing crude methyl methacrylate (MMA) stream which contains methacrylic acid, methacrylamide (MAM), methanol, and a sulfur acid salt and contains an organic component containing methyl methacrylate, the method comprising:

including in the organic component of the sulfur acid containing crude MMA stream one or more N-oxyl compound polymerization inhibitor.

2. The method as claimed in claim 1, wherein the sulfur acid salt is a sulfuric acid salt or a sulfonic acid salt, and the salt is an ammonia, or alkali metal salt.

3. The method as claimed in claim 1, further comprising:

neutralizing the sulfur acid containing crude MMA stream to generate a two phase stream having a neutralized aqueous component containing at least the sulfur acid salt, a methacrylic acid salt, methacrylamide (MAM), water and methanol, and an organic component containing methyl methacrylate, followed by;

including in the neutralized aqueous component, or the organic component, or both, one or more N-oxyl compound polymerization inhibitor effective in both the aqueous component and the organic component, followed by;

separating the neutralized aqueous component from the organic component, thereby forming a treated crude MMA stream and, separately, a neutralized aqueous stream which comprises a methacrylate salt.

4. The method as claimed in claim 1, wherein the polymerization inhibitor is 4-hydroxy-2, 2, 6, 6-tetramethylpiperidinoxyl (4-HT).

5. The method as claimed in claim 3, wherein the including of the polymerization inhibitor further comprises adding a second inhibitor chosen from hydroquinones; aromatic amines; thiazine containing compounds; nitrosophenols; 4-hydroxy-2,3,6,6-tetramethylpiperidine; and mixtures thereof, to the neutralized aqueous component, to the organic component, or to both.

6. The method as claimed in claim 3, wherein the neutralizing comprises adding aqua ammonia to the two-phase feed stream and the resulting pH ranges from 6 to 10.

7. The method as claimed in claim 3, wherein the amount of the N-oxyl compound polymerization inhibitor added to the neutralized aqueous component, to the organic component, or to both, ranges from 10 to 5000 ppm, based on the total weight of the component to which it is added and the total polymerization inhibitor.

8. The method as claimed in claim 3, wherein neutralizing comprises adding aqueous ammonia, the method further comprising removing the neutralized aqueous stream comprising methanol, MAM and ammonium methacrylate ($NH^{4+}MAA^{-}$) after separating the organic component and the neutralized aqueous component of the two phase stream, thereby providing the treated crude MMA stream.

9. The method as claimed in claim 3, further comprising washing the treated crude MMA stream that contains the N-oxyl inhibitor a second time with water, or multiple times with water, following by including additional N-oxyl compound polymerization inhibitor after each successive washing.

10. The method as claimed in claim 1, wherein, wherein the sulfur acid containing crude MMA stream contains less than 1000 ppm of an azeotroping solvent or entraining solvent.

* * * * *